United States Patent [19]

Reese

[11] Patent Number: 5,595,172
[45] Date of Patent: Jan. 21, 1997

[54] SUCTION STYLET FOR USE WITH AN ENDOTRACHEAL TUBE

[76] Inventor: John L. Reese, 2416 W. Bayshore Rd., Gulf Breeze, Fla. 32561

[21] Appl. No.: 289,207

[22] Filed: Aug. 12, 1994

[51] Int. Cl.⁶ .................................................. A61M 16/00
[52] U.S. Cl. ................ 128/200.26; 128/207.14; 128/207.15; 128/207.16
[58] Field of Search ................ 128/200.26, 207.14, 128/207.15, 207.16

[56] References Cited

U.S. PATENT DOCUMENTS

| | | | |
|---|---|---|---|
| 4,502,482 | 3/1985 | DeLuccia et al. | 128/207.15 |
| 4,512,765 | 4/1985 | Muto | 604/119 |
| 4,699,138 | 10/1987 | Behrstock | 128/207.16 |
| 4,846,153 | 7/1989 | Berci | 128/200.26 |
| 5,000,175 | 3/1991 | Pue | 128/207.14 |
| 5,016,614 | 5/1991 | MacAllister | 128/4 |
| 5,257,620 | 11/1993 | Schermerhorn | 128/200.26 |
| 5,329,940 | 7/1994 | Adair | 128/200.26 |

*Primary Examiner*—Aaron J. Lewis
*Attorney, Agent, or Firm*—Beveridge, DeGrandi, Weilacher & Young, LLP

[57] ABSTRACT

A suction stylet suited for use with an endotracheal tube. The stylet has a main body with a central passageway which extends along the length of the main body. The central passageway is in fluid communication with a suction source at one end and in fluid communication with an elongated suction stylet extension at an opposite end. The extension has a free end with a suction port or ports. The main body also includes a connector member for releasable attachment with an endotracheal tube. When connected, the stylet extension's free end is near the free end of the endotracheal tube. A vent arm extends off of the main body and includes a vent passageway that opens into the central passageway, preferably at an angle of 90° or less. The vent arm extends toward the free end of the extension and features a vent port at its end that opens into the vent passageway. The vent port is positioned so as to be easily closed by a finger of an operator who is grasping the stylet with the same hand. When the vent port is open, there is essentially no suction drawn at the free end of the extension. When the vent port is closed, sufficient suction is provided at the free end of the extension for removing fluids present in the trachea region of a patient. The main body has both a downward and a side bend formed along its length to place the suction tubing out of the line-of-sight and to avoid twisting of the suction tube. A preferred bend angle is 25°–50°, or more preferably 30°–45°.

27 Claims, 5 Drawing Sheets

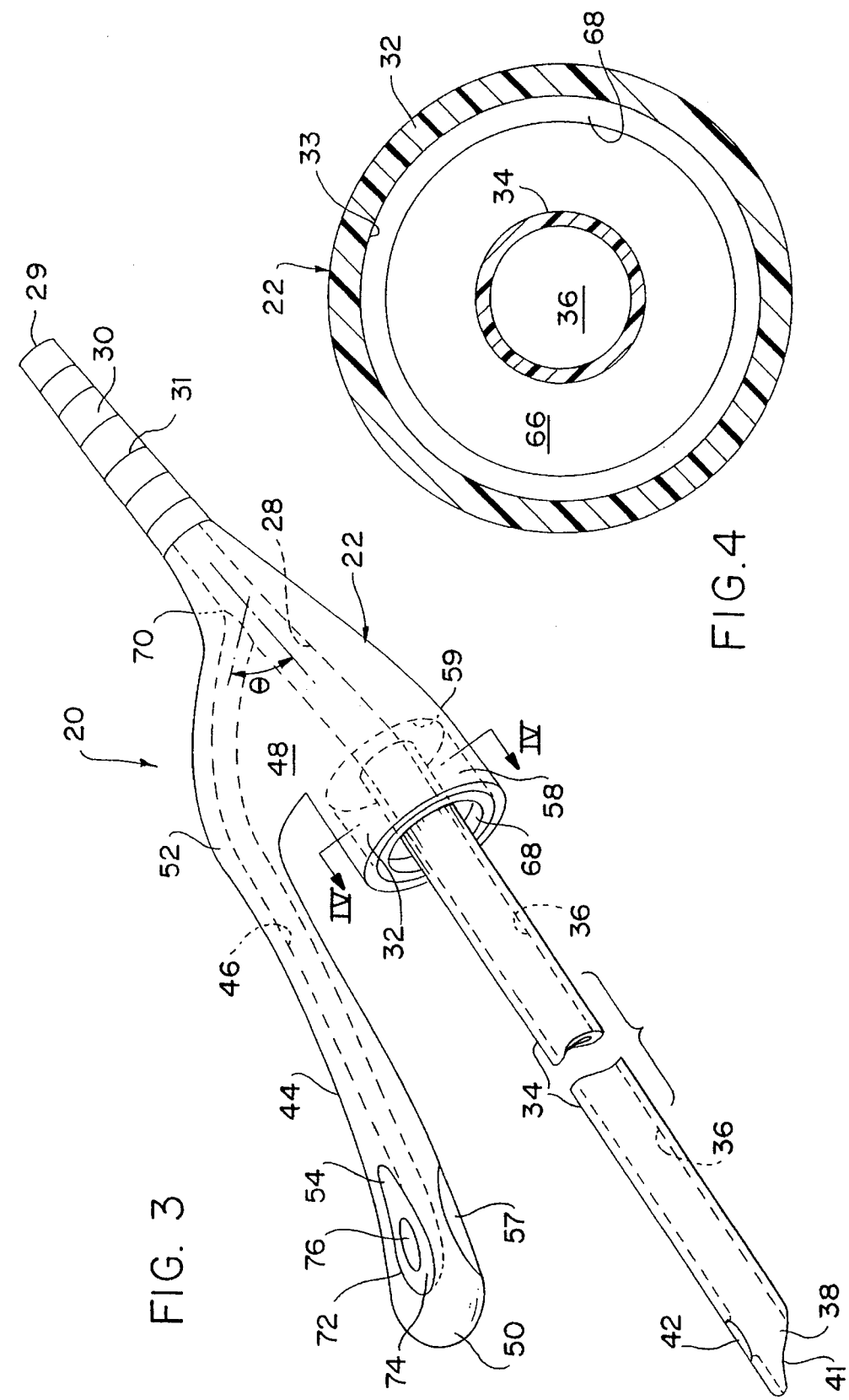

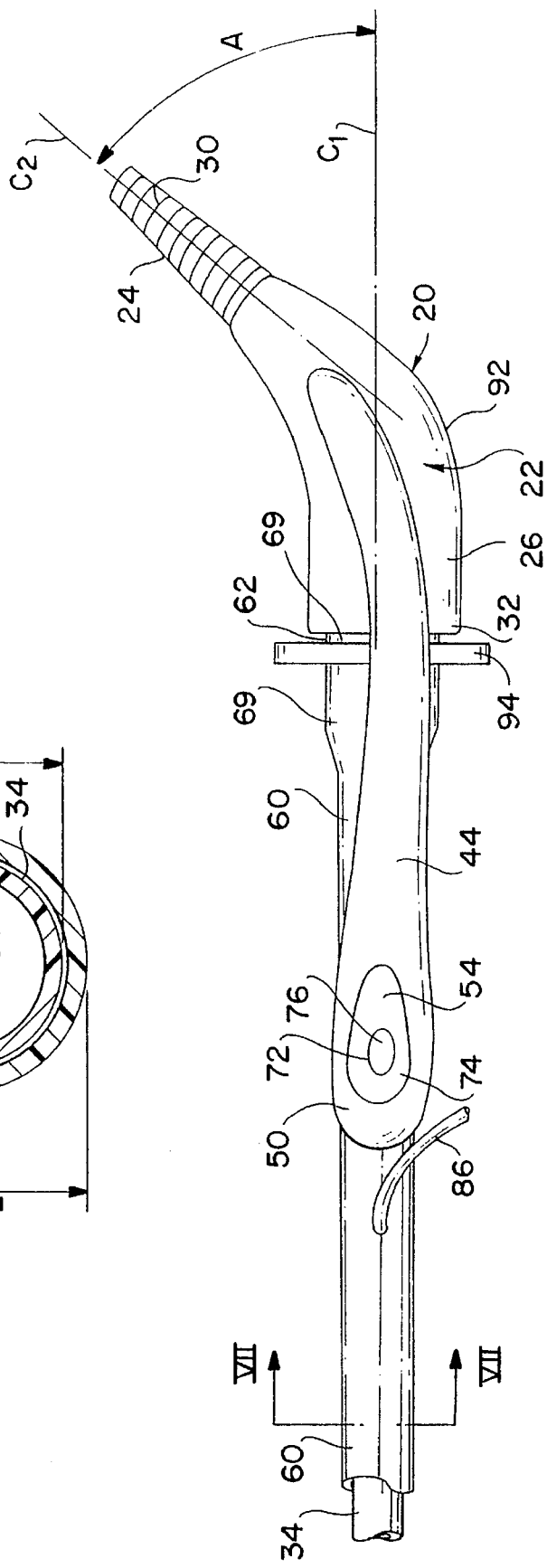

SUCTION STYLET FOR USE WITH AN ENDOTRACHEAL TUBE

CROSS REFERENCES

This application corresponds with Disclosure Document No. 340716 filed in the U.S. Patent and Trademark Office on Oct. 13, 1993. This Disclosure Document is incorporated herein by reference.

FIELD OF THE INVENTION

The present invention relates to a suction stylet for use with an endotracheal tube. More specifically, the present invention is directed at a suction stylet which is adapted for connection with an endotracheal tube and which has means for controlling the application of suction at the inserted end of an endotracheal tube.

BACKGROUND OF THE INVENTION

In many medical situations it is important to maintain a clear breathing passageway such that oxygen is continuously supplied to the brain. Maintenance of the clear passageway is often achieved through the placement of an endotracheal tube into the trachea such that an uninterrupted passageway exists between the patient's lungs and the oxygen environment. To facilitate insertion of an endotracheal tube, a doctor, paramedic or other medical professional will often rely on a laryngoscope blade which is inserted down the patient's throat and helps the treating person properly position the endotracheal tube.

Even with the help of the laryngoscope blade, however, it is often still difficult to properly insert the endotracheal tube due to vomit, oral secretions and blood blocking the inserter's vision. In an effort to overcome this problem, medical personnel often first insert suction tubes prior to insertion of the endotracheal tube. This additional insertion of a suction tube increases the time involved in the proper placement of the endotracheal tube. This added time presents a serious health risk as often the insertion of the tube within the minimum time possible is desirable to avoid anoxia. Moreover, even when the suction tube is first inserted, it is possible for the vision blocking fluids and debris to return between the time of suction tube removal and endotracheal tube insertion.

U.S. Pat. No. 5,257,620 describes an apparatus and method for endotracheal tube intubation which features an endotracheal tube with a suction stylet telescopically disposed therein and releasably fixed to the endotracheal tube. This tube is connected to a suction source such that when the suction source is operating fluid is drawn up continuously into the open end of the stylet. Thus, suction forces can be present during insertion of the tube and stylet combination, following insertion of the combination, and during removal of the suction tube. The presence of a suction at the tip of the combination throughout the insertion stage of the introduction process is problematic from the standpoint that there are times when it is desirable not to have suction during that stage. For instance, when the endotracheal tube and stylet are placed between the vocal cords and into the larynx, there is the danger of damaging the cords and other structures if suction is placed on them and the endotracheal tube and stylet are then advanced or retracted.

SUMMARY OF THE INVENTION

The present invention is directed at a suction stylet for use with an endotracheal tube that not only avoids the requirement of inserting a tonsil suction instrument and an endotracheal tube at different times, but also allows an operator to control with precision the periods within which suction is provided at the free end of the suction stylet. The present invention also avoids having to utilize the semi-rigid piece of metal (often referred to as a stylet) that is used to aid in shaping the otherwise highly, flexible limp endotracheal tube.

In addition, the suction can be controlled easily and without distracting the inserter of the endotracheal tube. Further, insertion of both the tube and stylet can be done without blocking the view of the person inserting the combination of endotracheal tube and suction stylet. Furthermore, the present invention provides an improved holding area which allows for easy manipulation of the stylet and avoids the development of torsion in the suction tube leading to the stylet due to twisting of the suction tube line.

The present invention features a suction stylet that has a main body with a first end, a second end and an internal passageway extending between the first and second ends. The main body further comprises a suction fitting at the first end that is adapted for connection with a suction source and is positioned such that the internal passageway is in fluid communication with the suction source. The main body also includes a connector member at the second end which is adapted for connection with an endotracheal tube. The suction stylet also includes a suction stylet extension or lumen extending off of the second end of the main body. The suction stylet extension is adapted for insertion into the endotracheal tube and has an internal conduit which opens out at its free end. The opposite end of the suction stylet extension is positioned so that its internal conduit is in fluid communication with the internal passageway in said main body.

The suction stylet also features a vent arm that extends off from the main body. The vent arm has a first end or base connected with said main body and a second, free end spaced from the first end. The vent arm further includes a vent passageway extending between the first and second ends of said vent arm. A vent port that opens into the vent passageway is provided near the free end of the vent arm. The vent passageway opens into the internal passageway in a manner which avoids obstructing the flow of fluids and other suctioned materials travelling within the internal passageway. For example, the edge defining the end of the vent passageway opening into the internal passageway is flush with the surface defining the internal passageway and the passageway extends at an acute angle in a direction opposite to the suction flow.

The main body and suction stylet extension are arranged such that the internal passageway of the main body and the internal conduit of said suction stylet extension have a common central axis at their point of connection. The passageways also have the same diameter at least at their point of connection and are either straight or smoothly curved so that fluids and debris can easily pass through the stylet to an appropriate waste site.

The natural state of an endotracheal tube is slightly curved; however, the suction stylet of the present invention has no real natural state as it is formed of a malleable material which retains whatever shape given to it. Preferably, the stylet is provided with essentially the same shape as the endotracheal tube to facilitate insertion. The main body of the present invention is preferably formed of an essentially rigid material as it is positioned at the end of the endotracheal tube and therefore need not conform to any particular component and because it is desirable to maintain a relatively consistent position for the main body component, especially the vent arm.

As noted, the vent passageway of the vent arm extends away from the internal passageway at an acute angle. Also, the vent arm extends off from the main body such that the free end of the vent arm and the vent port are closer to the second end of the main body than to the first end of the main body. The vent port is positioned such that the operator can extend his or her index finger and block the vent port so as to achieve suction at the free end of the suction stylet extension. The vent blocking or releasing finger is of the same hand that is comfortably grasping or pinching the vent arm and/or main body.

The vent arm has a concavity along of its length which conforms with the natural concave curvature in the endotracheal tube. Also, the vent arm and endotracheal tube extend out away from the main body in alignment. That is, if the main body is positioned such that the vent arm is on top, a vertical plane bisecting the vent arm would bisect the underlying endotracheal tube.

The main body is formed so as to have both a side bend and a downward bend. The downward bend places the suction tube connecting end of the main body lower than the opposite end of the main body such that the suction tubing hangs downward directly off the suction tube connecting end rather than having to run upward in looped fashion into connection with the suction tube connecting end. This arrangement avoids the formation of kinks and the like in the suction tubing. In addition to the downward bend, the suction end of the main body bends away to one side (e.g., to the right side for a right handed user and to the left side for a left handed user). The bend to the side directs the suction tubing out of the line of sight of the person installing the combination.

In normal use the vent arm is basically on the top of the tube, the thumb is on the left of the vent arm, the index finger is on the top of the vent arm on the vent port, the middle finger is on the right of the vent arm, the ring finger is supporting the endotracheal tube and all fingers are squeezing together to maintain the vent arm and endotracheal tube as a single unit during insertion. The main body rests against the first web space of the user (the space between the thumb and index finger). During insertion and removal the usual line-of-sight is between the thumb and index finger to the end of the tube and therefore the combinations— configuration and the hand position with respect to that configuration provide a clear line-of-sight during insertion, either with or without the assistance of a laryngoscope. As discussed in greater detail below, this gripping method essentially allows for instantaneous on/off manipulation at the end of the suction stylet extension, since the index finger needs only to move on or off the vent arm port to discontinue suction at the stylet extension tip. When the finger is removed, the suction air will be drawn in from the vent arm port and passageway which offers less resistance than the suction stylet extension.

Preferably, the connector member of the main body includes a cylindrical extension with a free end adapted to extend over or under and frictionally retain the end of the endotracheal tube. The suction stylet extension is preferably provided with a cross-sectional exterior circumference that is less than that of the free end of the cylindrical extension and less than the internal conduit of the endotracheal tube such that the suction stylet extension is able to extend internally within the endotracheal tube when the cylindrical extension is frictionally engaged with the endotracheal tube. The connector member can include a friction enhancing ridge of the same material or a more elastic material or the connector member may be provided with some other connector means such as a rotatable key-key slot arrangement which allows for temporary rigid interlocking with the endotracheal tube and stylet in the proper orientation. The friction form of interconnection is desirable from the standpoint it is often required that the suction stylet be withdrawn quickly after the endotracheal tube is inserted to initiate oxygen flow to the brain.

The suction stylet extension is preferably circular in cross-section with an external diameter less than that of the interior surface defining the internal conduit in the endotracheal tube. The connecting end of the endotracheal tube is thus inserted between the exterior of the suction stylet extension and the interior of the connector member. The suction stylet extension is dimensioned so as to extend nearly to the beveled, open end of the endotracheal tube and includes an open distal end and an additional side port adjacent the distal opening. The side port of the extension is positioned to correspond with the side port often provided in endotracheal tubes.

An additional advantage of having two ports at the end of the suction stylet extension is that should one of the ports become occluded by a large piece of debris, the other will continue to function. Also, the two ports are at right angles so that it is unlikely that they would contact the same thing. Another very strong advantage of having two suction ports is that with only one it would be very easy to suck a piece of tissue against the tube, and if this tissue occluded the single port, the full suction would be applied to it and this alone could damage it, or it could be ripped away by movement of the stylet. With two ports, this is much less likely to ever occur. For instance, if one suction port attaches to tissue (e.g., the vocal cord), the tissue would only experience gentle suction as the other port would continue to suction air/fluids and thus relieve the suction of the occluded port. This provides a safety factor which is in addition to the added safety factor of being able to easily discontinue the suction by temporarily releasing the index finger from a vent port of the vent passage provided in the vent arm. Thus, during insertion or the like the suction can be released temporarily anytime it is felt that tissue has become secured to the suction port.

In a preferred embodiment, the suction stylet extension, when operationally positioned, is recessed from the end of the endotracheal tube a distance of 1 to 5 mm. This recessed positioning further protects the patient from traumatic contact with the end of the stylet extension during intubation as tissue is less likely to be drawn into contact with the suction stylet extension in the ports.

In a preferred embodiment the entire suction stylet including suction stylet extension, main body and vent arm are integrally formed as a single unit and of a common material. Due entirely or mainly to the differences in thickness of the material defining the main body and the suction stylet extension, the main body and vent arm are relatively rigid while the suction stylet extension is semi-rigid or flexible (e.g., malleable).

The suction fitting provided at the end of the main body can take any form that can be interconnected with a suction source so as to provide a releasable, but secure connection between the suction source's tubing and the main body. A suction fitting that is elongated, ribbed and in the form of a tapering cylinder and which extends along a central axis of the internal passageway and has a maximum diameter less than that of a central portion of the main body is suitable.

The vent arm preferably has a base which is positioned intermediate of the first and second ends of said main body and extends directly off from the side of the main body. In addition, the vent arm has an outer extension portion and the aforementioned intermediate concave bent portion.

To allow an operator to easily locate a finger over the vent port, the vent port features a boundary edge formed in the vent arm, a concave shaped side wall or depression extending inwardly into the vent arm, and an aperture formed in a deeper region of the concave wall and opening into the vent passageway. This design allows an operator to readily locate the aperture by feel, which can be important as an operator is often visually concentrating on a different area during insertion and use of the stylet. The design also provides an effective way to make sure the vent port is closed when desired. Further, the operator is able to continue grasping the combination suction stylet and endotracheal tube while the suction is being manipulated.

The free end of the vent arm also preferably further includes a pair of depressions formed on opposite sides of the vent port. These depressions are positioned such that the operator's thumb and third finger may rest snugly against the vent arm. With this positioning of the fingers, which approximates the finger positioning of a pencil grip, the suction stylet can be stabilized and easily manipulated during use.

The invention is also directed at the combination of a suction stylet having the characteristics described above and an endotracheal tube having a first open end and a second open end and an internal conduit therebetween.

The present invention is further directed at a method of endotracheal intubation which comprises grasping a suction stylet having an elongated extension that features a suction port or ports at its free end, an internal conduit in communication with the suction port and an open second end. The grasped stylet further includes a main body with second open end extending from one end of the main body and opening into the second, open end of the extension. The grasped stylet further comprises a vent arm extending off from the main body with a vent passageway formed therein which opens into the internal passageway at one end and, at an opposite end, into a vent port formed at a free end of the vent arm.

The method further includes inserting the extension of the suction stylet into a conduit of an endotracheal tube until one end of the endotracheal tube releasably interconnects with a connector forming part of the suction stylet and a free end is positioned at or immediately adjacent the free end of the endotracheal tube.

In addition, the method includes inserting the endotracheal tube and connected suction stylet into a patient in an intubation process and drawing fluid through the suction port(s), down the extension and through the main body by holding the stylet (e.g., main body and/or vent arm) and endotracheal tube with one hand while positioning a finger of that same hand over the vent port so as to direct the suction forces to the end of the extension. In addition, the method includes temporarily discontinuing essentially all suction at the end of the suction stylet and then reapplying the suction during the insertion of the combination.

The present invention will be more fully understood from the detailed described below and the accompanying drawings which are given by way of illustration only and thus are not meant to limit the present invention and wherein:

BRIEF DESCRIPTIONS OF THE DRAWINGS

FIG. 3 shows another perspective view of the suction stylet which is cutaway and in greater detail;

FIG. 4 represents a cross-sectional view taken along cross-section line IV—IV in FIG. 3;

FIG. 6 represents a cutaway top plan view of the combination shown in FIG. 5;

FIG. 7 represents a cross-sectional view taken along cross-section line VI—VI in FIG. 6.

DETAILED DESCRIPTION OF THE PREFERRED EMBODIMENTS

Figure 1:
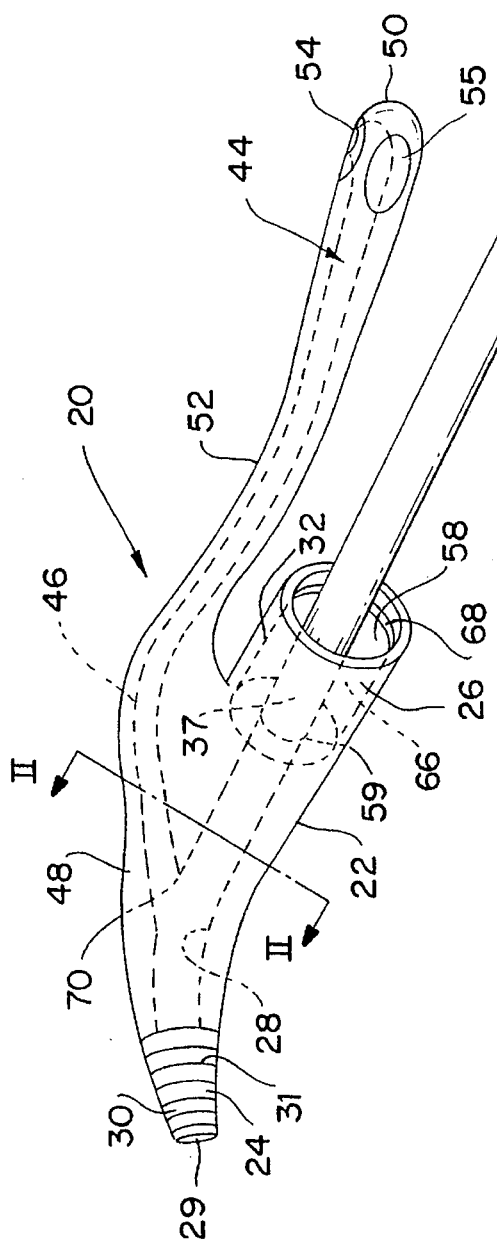
FIG. 1 shows a perspective view of the suction stylet of the present invention.

FIG. 1 illustrates a perspective view of a preferred embodiment of suction stylet 20. Suction stylet 20 includes main body 22 having first end 24 and second end 26. Internal passageway 28 extends between ends 24 and 26 of main body 22. Suction fitting 30 is provided at the first end of main body 22 and is hollow so as to form a portion of internal passageway 28. Suction fitting 30 has opening 29 as well as ribs 31. The ribs 31 help provide a good friction connection between suction fitting 30 and suction tubing 78 (FIG. 5) which extends from a suitable suction source (not shown). Opening 29 thus opens into the tubing 78 of the suction source.

Second end 26 of main body 22 is provided with connector member 32. Connector member 32 includes cylindrical extension 58 with internal hollow 66 defined by backing member 59 and the interior surface of cylindrical extension 58. Connector member 32 is also shown to include friction enhancing ridge 68.

Suction stylet extension or lumen 34 extends off from backing wall 59 at first end 37 and terminates at free end 38. Suction stylet extension 34 includes internal conduit 36 which opens into internal passageway 28 at backing wall 59. Backing wall 59 forms the internal back wall of hollow 66 which is further defined by the interior surface 33 (FIG. 4). At free end 38, the extension's internal conduit 36 opens out at the very tip and also at side port 42 which side port is preferably spaced so as to have a downstream edge corresponding with the upstream edge of the angled opening at free end 38 (see FIG. 3).

Endotracheal tubes are currently provided in a range of different sizes, given in millimeters of internal diameter; e.g., an 8 millimeter endotracheal tube will have an 8 mm internal diameter. These tubes come in different sizes to accommodate different size people. An adult male typically requires a number 8 or 8.5 tube, an adult women a size 7, and a child possibly a size 4. The different size endotracheal tubes also have different lengths, which are generally not specified on the market, but are consistent between tubes of the same size. The present invention has various sizes that correspond with the various sizes for the endotracheal tubes. For example, a size 7 sectioning stylet to fit into a size 7 endotracheal tube and a size 8.5 suction stylet to fit into a size 8.5 endotracheal tube. Presently there is about 12 sizes with only about 4 common adult sizes.

FIG. 1 shows vent arm 44 extending off from main body 22 intermediate first and second main body ends 24 and 26. Vent arm 44 includes base section 48 which is integrally joined with main body 22. Vent arm 44 also includes intermediate bent (concave) section 52 positioned between base section 48 and free end section 50. The vent arm extends away from suction fitting 30 and toward the free end 38 of suction stylet 34. The free end section 50 of vent arm 44 thus extends over and past connector member 32 and longitudinally along a portion of extension 34. Vent arm 44 extends longitudinally for about 10 to 14 cm and, more preferably, 12 cm. Extension 34 is shown in an uncurved state in FIG. 1, but because it is formed of a malleable material it preferably is provided with a concave shape corresponding to both the endotracheal tube into which it is to be inserted and the curved vent arm.

Vent arm 44 has vent passageway 46 formed therein. Vent passageway 46 extends from finger port 54 and opens into internal passageway 28 at its opposite end. Edge 70, defining the open end of vent passageway 46, is formed with respect to internal passageway 28 so as not to interrupt the fluid flow along passageway 28. In fact, passageway 28 shares a common central axis at bottom wall 59 with internal conduit 36 and is in line with the straight internal conduit 36 shown in FIG. 1.

FIG. 1 also illustrates grasping recess 55 which is placed to one side of finger port 54. A similar grasping recess 57 is positioned on the opposite side of finger port 54 at the vent arm's free end 50 (see FIGS. 3 and 5). During certain periods of the intubation and removal process, it is desirable to grasp the combination suction stylet and tube in a pencil like grip. The pencil like grip involves placing one's thumb and third fingers in depressions 55 and 57 so as to pinch the free end of the vent arm while the index is over the vent port. The remaining free fingers are used to pinch the vent arm and endotracheal tube together into a common unit. Also, the web provided between the index finger and thumb rests on the main body and is positioned so as to be aligned with the line-of-sight used in inserting or removing the combination. Manipulation of the combination can thus be done by shifting the pinched vent arm and entubation tube while still controlling suction with the index finger. The frictional contact between the endotracheal tube and suction stylet maintains the two components secured together so that they rotate or shift as a unit during the intubation process. The aforementioned grip is generally used only for the purpose of insertion which is the most difficult and critical component of the intubation process. Once inserted, a balloon (see FIG. 5) provided at the end of the endotracheal tube is inflated to fix the tube into position and to allow for the careful removal of the suction stylet. Rotation or movement of the combination would typically only occur in an attempt to suck out debris or to reach an opening between the vocal cords.

Figure 2:
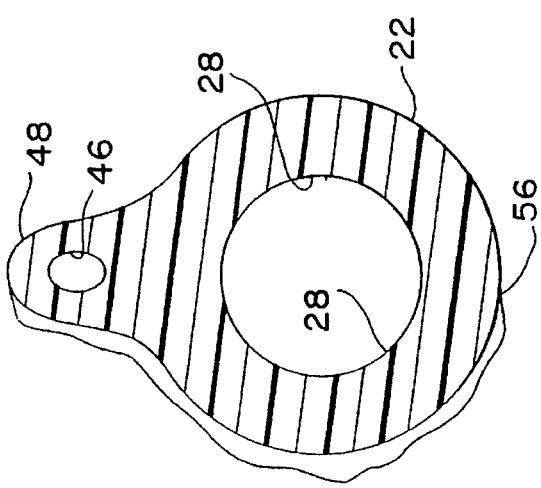
FIG. 2 shows a cutaway, cross-sectional view taken along cross-section line II—II in FIG. 1.

FIG. 2 illustrates a cross-section through base 48 of vent arm 44 and through the central portion of the main body defining internal passageway 28. As shown in FIG. 2, the vent arm and remainder of the main body are formed of a solid integral body of preferable a semi rigid or rigid plastic. Other variations are also contemplated such as forming the vent arm and remainder of the main body as separate, attachable units of the same or different material.

FIG. 3 provides a cutaway, perspective view of the suction stylet shown in FIG. 1. As can be seen from FIG. 3, the free end 38 has beveled free end opening 41 as well as side suction port 42. FIG. 3 also provides a more detailed illustration of finger vent port 54. As shown in FIG. 3, vent port 54 includes external boundary 72 from which extends concave sidewall or depression 74 with aperture 76 formed in the lowest region of depression 74.

FIG. 3 also illustrates the manner in which vent passageway 46 opens into internal passageway 28. The portion of vent passageway 46 extending within base 48 has a central axis which forms an acute angle with respect to the central axis of the portion of internal passageway 28 into which passageway 46 opens. This acute angle is designated by θ and preferably ranges from 5 to 80 degrees. This arrangement helps avoid fluid and debris from inadvertently passing up into the vent passageway as the fluid and debris are drawn down conduit 36 and through internal passageway 28. After passing through internal passageway 28, the fluid and other waste material is drawn along suction tubing 78 to a suitable disposal means (not shown).

FIG. 4 provides a cross-sectional view taken along cross-section line IV—IV in FIG. 3. As shown in FIG. 4, connector member 32 includes interior surface 33 which shares a common central axis with suction stylet extension 34. As explained in greater detail below, interior surface 33 has a diameter which is similar to the exterior external diameter of bulbous section 69 of endotracheal tube 60 (see FIG. 6) which forms end 62 of endotracheal tube 60. As shown in FIG. 4, internal hollow 66 is formed between the exterior surface of suction stylet extension 34, the interior of connector member 32 and backing wall 59.

To facilitate the interconnection of ends 62 of the endotracheal tube with connector member 32, friction enhancing ring 68 is provided near the free end of connector member 32. Ring 68 can be either formed of the same material as the remainder of connector member 32 and provided with a smaller interior diameter than surface 33 so as to deform during insertion over bulbous member 69 or it can be formed of a ring of elastomeric material added on by adhesive or the like. The connector member is designed for frictionally retaining an endotracheal tube such as a 15 mm fitting for a standard endotracheal tube.

Suction stylet 20 is preferably formed as a unitary member in a molding operation. The molded stylet is thus preferably formed of the same material which can be any material suitable for medical use. Suitable materials include those commonly used in the industry for disposable medical devices. The vent arm, suction fitting, main body and suction stylet extension can also be formed of different materials and appropriately connected together (e.g., the suction stylet extension formed of a more flexible plastic than the main body, vent arm and suction fitting). In order to achieve its required function, however, suction stylet extension 34 is formed of a material that will not collapse under typical suction settings and is of a type of material which will prevent the internal conduit of the suction stylet extension from becoming occluded when the extension is bent or otherwise deformed during use.

Another preferred embodiment of suction stylet 20 is formed of a material (e.g., a flexible plastic with structural elements such as a wire mesh or individual wires internally molded within the suction stylet extension body) that enables the suction stylet (or at least the suction stylet extension) to retain its shape subsequent to a predetermined shape deformation. In other words, the stylet or stylet extension is formed of a malleable material having sufficient rigidity to hold the endotracheal tube in the new configuration of the deformed stylet. This makes it possible for the suction stylet to function with a deformable endotracheal tube that can be deformed into useful shapes and held in that shape by the stylet so as to facilitate endotracheal intubation.

Figure 5:
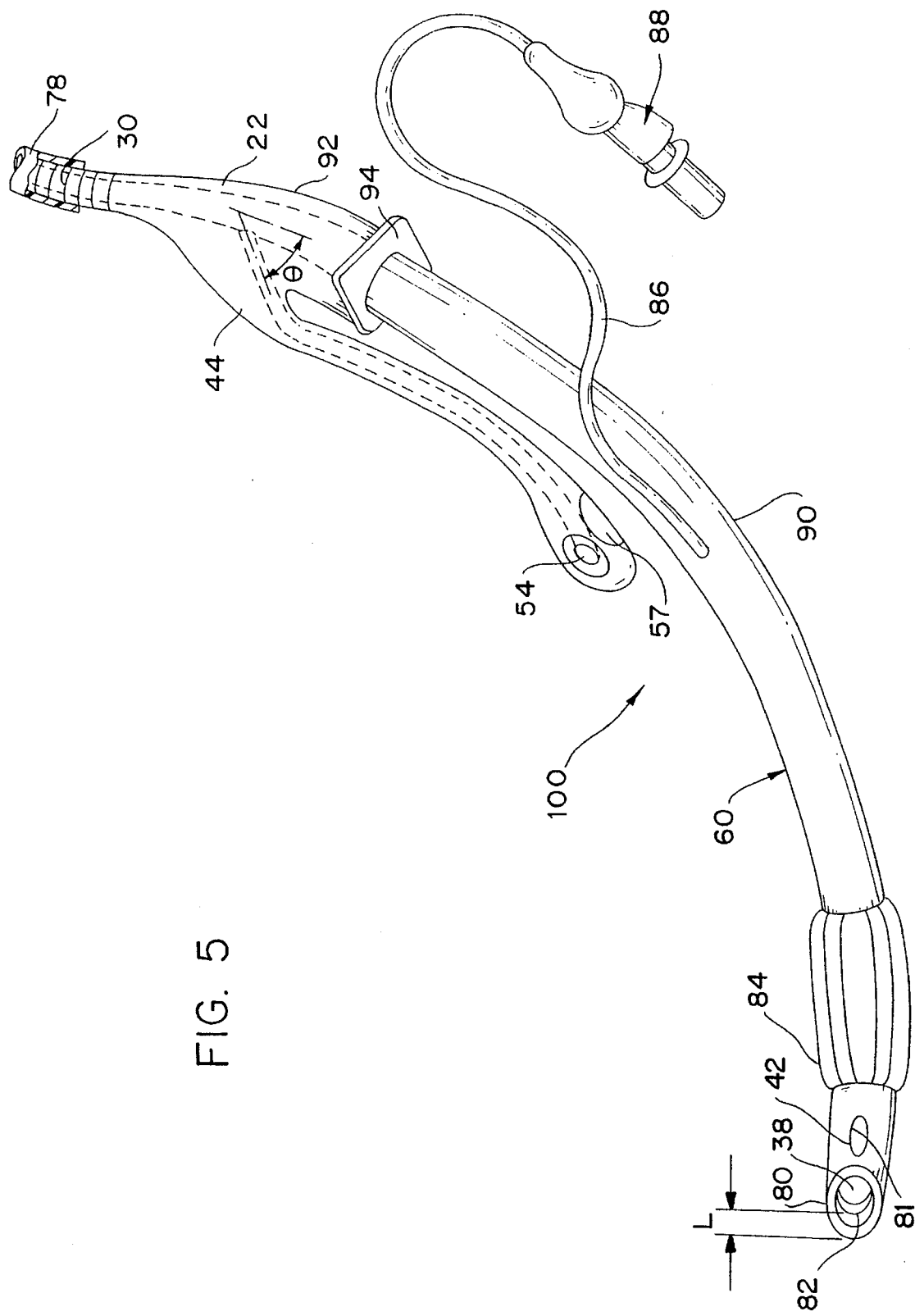
FIG. 5 shows a perspective view of the suction stylet of FIG. 1 in combination with an endotracheal tube.

FIGS. 5 and 6 illustrate the suction stylet and endotracheal tube combination of the present invention. Combination 100, comprised of suction stylet 20 and representative endotracheal tube 60, allows the operator to apply suction to the end of endotracheal tube 60 in order to aspirate oral/pharyngeal contents or debris such as blood and vomitus, without releasing the endotracheal tube. The combination is first inserted into the mouth and pharynx where the debris is suctioned out so that the vocal cords can be visualized, as they are in the opening of the larynx and are the difficult part to see and to insert the combination through. Final placement is achieved when the endotracheal tube passes through the vocal cords into position within the larynx. One of the advantages of the present invention is that the suction at the tip can be controlled. The advantage of this control lies primarily in being able to stop suction when the tube is actually placed between the vocal cords and into the larynx. There is a danger of damaging the cords and other structures if suction is placed on them and the suction stylet then advanced. In the present invention the suction ports are recessed so as to avoid having the suction stylet, itself, come in contact with the vocal cords and other structures.

FIG. 5 further illustrates suction source tubing 78 which is sufficiently elastic for expansion and contraction about ribs 31 of fitting 32 so as to sealingly secure the suction fitting 30 to the suction tube. Alternatively, any other known fluid tight connection means may be utilized. The invention also contemplates providing a rotatable connection between the suction port connection and suction tubings so as to allow for rotation of the main body without generating torsion in the suction line.

The suction stylet is designed to control the shape of the more pliable endotracheal tube, although it is preferable that the suction stylet has an initial shape that is the same as the endotracheal tube to aid in the initial insertion of the suction stylet into the endotracheal tube. As shown in FIG. 5, suction stylet 20 and endotracheal tube 60 have a slight curvature 90. The material of the suction stylet extension allows it to deform to any shape an endotracheal tube might assume or might have in its purchased state. In addition, the stylet has sufficient rigidity to control and maintain a final shape in the endotracheal tube when the tube is deformed and designed so as not to maintain a deformed state.

The length of the suction stylet extension is designed such that the tip 38 extends nearly to free end 80 of endotracheal tube 60. As shown in FIG. 5, the tip of the suction stylet extension is beveled to conform with the beveled shape of the tip of the endotracheal tube which defines opening 82. The length of the suction stylet extension 34 is also preferably designed so as to have the tip recessed within the endotracheal tube in which it is to be used. This recessing of the tip lessens the possibility of exposure of the tip to anatomical structures during endotracheal intubation. Extension 34 also includes side suction port 42 which is positioned to coincide with the side port 81 of a standard endotracheal tube and provides an additional sight of suction. The use of a side suction port helps provide suction in areas where there is likely to be blocking fluid or debris and the opening at tip is not easily accessible. Additional side ports can also be provided to even further increase the scope of suction coverage. The amount that the bevelled tip of suction stylet extension 34 is recessed with respect to the bevelled end of endotracheal tube 60 is depicted in FIG. 5 as length L. Length L is preferably about 1 to 5 mm.

To help align the similarity shaped bevelled edges of the endotracheal tube and the suction stylet extension as well as their respective side ports, matchable indicia can be provided on main body 22 and on the connecting end of endotracheal tube 60. When the indicia is matched the operator can be assured of proper positioning of both the suction stylet within the endotracheal tube as well as the optimum position for vent arm 44.

FIG. 5 also illustrates endotracheal tube 60 having a standard inflatable member 84, inflation line 86 and inflation means 88. The free end of vent arm 44 is shown to extend essentially to the inlet port for the balloon inflation line.

FIG. 6 provides a top plan view of suction stylet 20 in combination with endotracheal tube 60 (hereinafter the "combination"). As shown in FIG. 6, vent arm 44 extends out away from main body 20 in an aligned fashion with respect to endotracheal tube 60 such that a plane bisecting vent arm 44 (i.e., transverse to the surface of the FIG. 6 drawing sheet) and extending vertically through the vent arm would bisect underlying tube 60.

FIG. 6 also shows a right side bend formed in main body 20 which helps provide a clear line-of-sight to a right handed user during intubation. A left side bend would be provided for left handed operators. The side bend provided in the main body also helps avoid the tendency for torsion to develop between the main body and the attached suction nozzle tube as the arrangement lessens the requirement for twisting the main body to provide an improved or different line of sight. The side bend is designated in FIG. 6 by angle A formed between lines C1 and C2. Line C1 extends generally along the central axis of connector 32 at end 26 of main body 20 while line C2 extends generally along the central axis of suction fitting 30. Angle A is preferably in the range of 20°–50° or more preferably 30°–45°.

Figure 8:
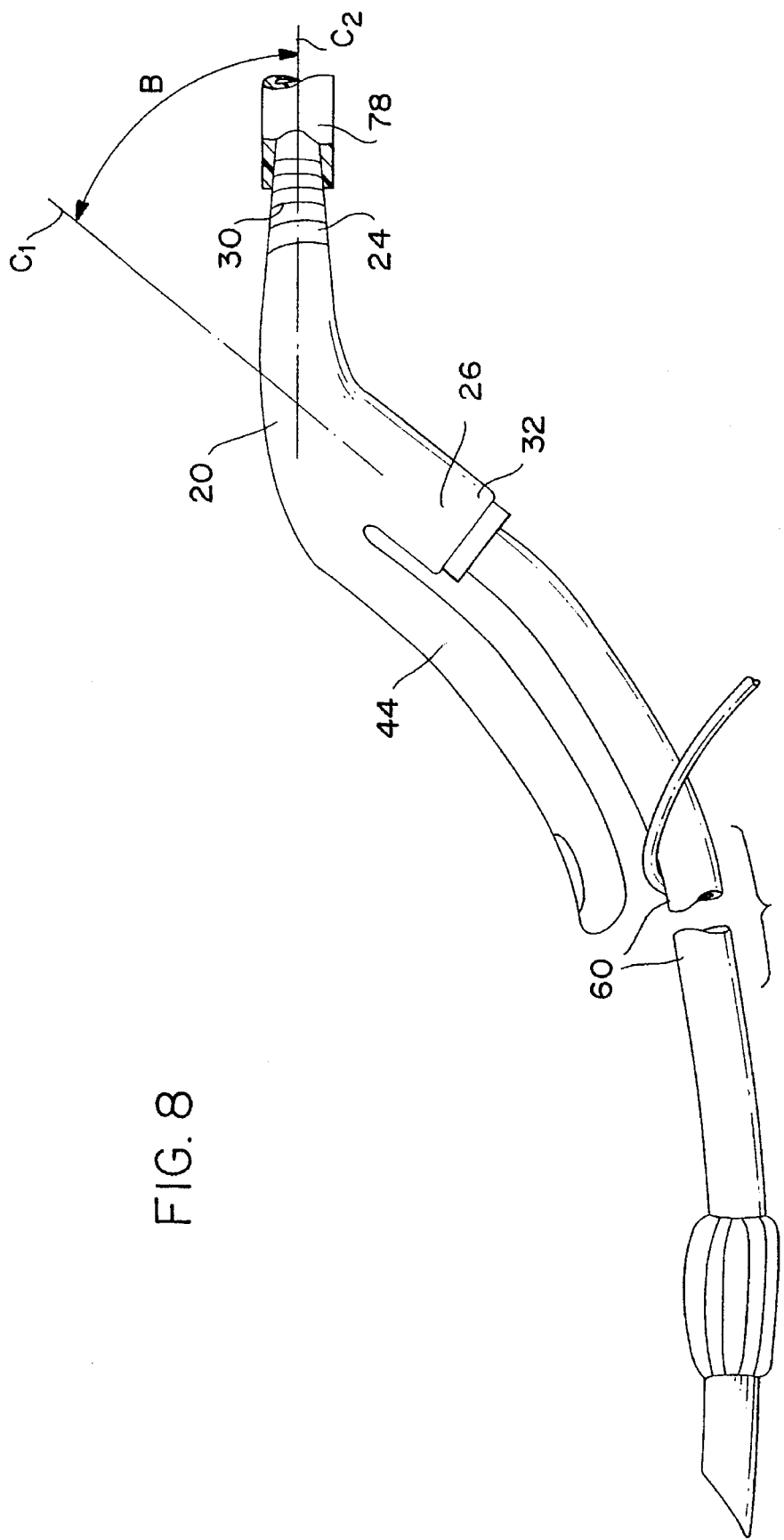
FIG. 8 shows a side elevational view of that which is shown in FIG. 6.

The side bend of angle A works in conjunction with a downward bend in main body 20 to provide an advantageous arrangement in the present invention. FIG. 8 shows a side elevational view of that which is shown in FIG. 7 and the downward bend in main body 20 is visible in this view. The downward bend is designated by lines C1 and C2 in FIG. 8 with the downward bend angle being referenced as Angle B. Angle B is preferably from 20°–50° and more preferably 30°–45°. The downward bend positions the suction tube in a position which is out of the line-of-sight of the operator and which helps avoid twisting, bending or kinking of the suction tube with respect to the main body. The debris or fluid caught up in the suction is thus exited in an efficient fashion and with less chance of blockage.

FIG. 6 provides an illustration of connector member 32 of main body 22 extending over bulbous end 69 of tube 60. Stop flange 94 extends about bulbous end 69 to limit the degree to which main body 22 is inserted into the endotracheal tube.

FIG. 7 provides a cross-sectional view taken along cross-section VII—VII in FIG. 6. As shown in FIG. 7, the exterior of suction stylet extension 34 preferably has an external diameter D1 which is about equal to the diameter of the interior surface 65 of endotracheal tube 60 such that suction is concentrated along the interior 37 of suction stylet extension 34 and fluid and debris does not easily flow between the exterior of the extension and the interior of the endotracheal tube. This helps avoid unwanted contamination of the endotracheal tube with the suction fluid and debris. The relationship between the exterior surface of the extension and interior of the tube is preferably a sliding friction relationship so as to provide also for easy insertion and removal of the suction stylet with respect to the endotracheal tube.

In use, suction stylet extension 34 is inserted within the interior of endotracheal tube 60 and suction stylet 20 is connected with endotracheal tube connector member 32. The suction stylet is adjusted to be in the correct position with respect to an endotracheal tube. The correct positioning can be achieved with or without the assistance of marking indicia or molded protrusions. Although various other connection means can also be relied upon, the one illustrated in the drawings represents a preferred embodiment as it is one that can readily be used with existing endotracheal tubes and in some instances it is desirable to allow for rotation of the stylet with respect to the tube while these two are connected.

Once appropriately combined, the combination is positioned for initial intubation. Suction stylet 20 is constructed in such a way that blockage of the vent port with the operator's index finger causes the suction stylet to act as a suction stylet device at the tip 38. This acts to clear the oral larynx and/or trachea of liquid and debris so as to facilitate endotracheal intubation. In addition, the positioning of the hand with respect to the main body 22 of the suction stylet and the positioning of the fingers in the pinched grasp position discussed above is such that the operator has a relatively clear field of vision for the intubation procedure.

Moreover, by taking off and reinserting the finger over the finger vent port, the operator is able to control the timing of suction at the tip of the hollow stylet. Thus, with the operator's index finger occluding the vent port, medical suction is transmitted to the tip of the hollow suction stylet extension allowing it to act as a tonsil suction device while avoiding contamination of the lumen of the endotracheal tube. When the operator's finger is off the vent port, the medical suction has a low resistance path through the vent arm and vent port to the atmosphere, thus allowing the suction stylet to act as a simple stylet and to be safely placed and moved within the trachea with controllable suction.

Although the present invention has been described with reference to the preferred embodiments, the invention is not limited to the details thereof. Various substitutions and modifications will occur to those of ordinary skill in the art and also substitutions and modifications are intended to fall within the spirit and scope of the invention as defined in the appended claims.

What is claimed is:

1. A suction styler, comprising:

a main body having a first end, a second end and an internal passageway extending in a direction between said first and second ends, said main body comprising a suction fitting with an opening that opens into the internal passageway and is adapted for connection with a suction source, and said main body further comprising a connector member which is adapted for connection with an endotracheal tube;

a suction stylet extension extending off of said main body and adapted for insertion into an endotracheal tube, said suction stylet extension having an internal conduit which opens out at a free end of said suction styler extension and, at an opposite end of said suction styler extension, is in fluid communication with the internal passageway in said main body;

a vent arm extending off from said main body, said vent arm having a first end connected with said main body and a second end spaced from said first end, said vent arm further including a vent passageway which extends in a direction between said first and second ends of said vent arm and opens into the internal passageway of said main body, and said vent arm further including a vent port which opens into said vent passageway.

2. The suction stylet of claim 1 wherein said suction fitting is provided at the first end of said main body and said suction stylet extension extends from the second end of said main body, and said main body having a downward bend which positions the first end of said main body at a lower position relative to said second end when said vent arm is in a top position.

3. The suction styler of claim 2 wherein said main body includes a side bend which positions the first end of said main body further away from a center line of said connector member than the second end of said main body.

4. The suction stylet of claim 3 wherein said downward bend and said side bend each form an angle of about 30° to 45°.

5. The suction styler of claim 1 wherein said main body includes a side bend which positions the first end of said main body further away from a center line of said connector member than the second end of the main body from which the suction styler extension extends.

6. The suction stylet of claim 5 wherein said side bend forms an angle of about 30° to 45°.

7. The suction stylet of claim 1 wherein the vent passageway of said vent arm extends away from said internal passageway at an acute angle, and in a direction opposite to an intended flow of fluid in said internal passageway.

8. The suction styler of claim 1 wherein said vent arm has a curved base and an outer section that extends essential parallel with said suction stylet and said vent arm is dimensioned such that the vent port is positioned at the second end of said vent arm and is closeable by a finger of an operator of said suction styler with such finger being of a same hand used for grasping, with other fingers of that same hand, said main body.

9. The suction styler of claim 1 wherein the vent passageway extends away from the first end of said main body and towards the free end of said suction stylet extension, and the vent port is positioned at the second end of said vent arm and is dimensioned so as to be closeable by a finger of an operator of said suction styler with such a finger being of a same hand used for grasping said main body with other fingers of that same hand.

10. The suction styler of claim 1 wherein said connector member includes a cylindrical extension having a free end that is adapted to frictionally retain an end of an endotracheal tube, and said suction stylet extension having a cross-sectional circumference which is less than that of the free end of said cylindrical extension such that said suction stylet is free to extend internally within a conduit in such an endotracheal tube when said cylindrical extension is engaged with such an endotracheal tube, and said suction stylet has an exterior diameter along its length which is dimensioned to be essentially the same as an internal diameter of such an endotracheal tube such that a sliding friction fit relationship is achieved.

11. The suction styler of claim 1 wherein said suction stylet extension is dimensioned so as to extend essentially to an open end of an endotracheal tube once said suction stylet is inserted in the endotracheal tube, and includes an open distal end and an additional side port adjacent the distal opening, and said side port being positioned so as to correspond with an endotracheal tube side port when positioned over said suction styler.

12. The suction stylet as recited in claim 11 wherein said suction stylet extension is dimensioned and arranged such that, when operationally positioned within an endotracheal tube, said extension has a free end that is within such an endotracheal tube and spaced 1 to 5 mm from an adjacent open end of such an endotracheal tube.

13. The suction stylet of claim 1 wherein depressions are formed in said vent arm and are spaced on opposite sides of the vent port and adapted for grasping by a tip of a third finger and thumb of an operator.

14. The suction styler of claim 1 wherein said vent arm and main body are integrally formed as a single unit and of a common material, and said internal passageway is defined by a wall surface of said main body and said vent passageway is formed of an internal wall surface of said vent arm.

15. The suction stylet of claim 1 wherein said suction stylet extension, main body and vent arm are integrally formed as a single unit and of a common, flexible material.

16. The suction stylet of claim 15 wherein said vent arm has a base which extends off said main body and has a convex upper surface section designed for contact with a web area of a person, which is provided between a thumb and first finger of such a person, and said vent arm includes an elongated body which extends out off from said base in cantilever fashion, and parallel with said suction styler when said suction stylet in an unbent mode.

17. The suction stylet of claim 1 wherein said vent arm has a base which is positioned intermediate of the first and second ends of said main body and an outer extension portion that extends essentially parallel with said suction stylet extension.

18. The suction stylet of claim 1 wherein said vent port features a boundary edge formed in said vent arm, a concave shaped side wall extending inwardly into the vent arm, and an aperture formed in a deeper region of the concave side wall and opening into the vent passageway.

19. The suction stylet of claim 1 wherein said suction stylet extension is formed of a material which is deformable into a deformed shape and retains that deformed state until later further deformed.

20. The suction stylet of claim 19 wherein said stylet includes strengthening structural material embedded within a flexible material outer coating.

21. An apparatus as recited in claim 1 wherein an internal suction conduit provided in said suction stylet extension shares a common central axis with said suction stylet extension.

22. An apparatus as recited in claim 1 wherein said suction fitting includes means for connecting said main body with an open end of a suction source tube.

23. An apparatus, comprising:
an endotracheal tube having a first open end, a second open end and an internal conduit extending therebetween;
a suction stylet having a main body with a suction fitting, a connector member, and an internal passageway extending therebetween, said suction stylet further comprising a suction stylet extension extending off from said main body and having an internal suction conduit which opens into the internal passageway of said main body, said suction stylet extension further including a free end with opening formed therein, said connector member being releasably connected to the endotracheal tube and said extension extending within the internal conduit of said endotracheal tube such that the free end of said extension is closer to the second end of said endotracheal tube than the first end, said suction stylet further comprising a vent arm extending off from said main body, said vent arm having a vent passageway that opens into the internal passageway of said main body and extends in a direction toward the free end of said extension, and said vent arm having a port formed therein which is positioned such that an operator grasping the stylet with one hand is able to close the vent port with a finger of that same hand.

24. An apparatus as recited in claim 23 wherein an external diameter of said suction stylet is essentially the same as an internal diameter of said endotracheal tube such that said suction stylet is received by way of frictional sliding contact within said endotracheal tube.

25. A method of endotracheal intubation, comprising:
grasping a suction styler with one hand, said suction styler including an elongated extension with internal suction conduit and a suction opening at a free end of the extension, said styler further including a main body with internal passageway extending from one end of said main body and opening into the internal suction conduit of said extension, said styler further comprising a vent arm extending off from the main body and having a vent passageway formed therein which opens into the internal passageway at one end and, at an opposite end, into a vent port formed at a free end of said vent arm;
inserting the extension of the suction styler into a conduit of an endotracheal tube until one end of the endotracheal tube releasably interconnects with a connector member forming part of the suction styler so as to form a combination structure; and
performing an intubation procedure with said combination structure while drawing fluid through the suction port and along the suction styler
(i) by holding the main body at a hand grasping area thereof designed for contact with fingers of one hand,
(ii) by pinching an end of said vent arm at a pair of finger reception areas if said vent arm which are designed for contact with fingers of the one hand and,
(iii) by closing off said vent by covering a vent port finger reception area designed for contact with a remaining finger of the one hand.

26. A method of endotracheal intubation as recited in claim 25, further comprising intermittently opening and closing the vent port by moving an index finger onto and off of the vent port.

27. A method as recited in claim 25 wherein said main body includes connecting means for connecting said main body with an open end of a suction source tube, and said method further comprising securing said suction source tube by inserting said connecting means into the open ends of the suction source tube.

* * * * *